United States Patent
Ayad

(10) Patent No.: US 7,153,279 B2
(45) Date of Patent: Dec. 26, 2006

(54) BRAIN RETRACTION SENSOR

(75) Inventor: Michael Ayad, Washington, DC (US)

(73) Assignee: George Washington University, Washington, DC (US)

( * ) Notice: Subject to any disclaimer, the term of this patent is extended or adjusted under 35 U.S.C. 154(b) by 129 days.

(21) Appl. No.: 11/016,818

(22) Filed: Dec. 21, 2004

(65) Prior Publication Data

US 2005/0228315 A1  Oct. 13, 2005

Related U.S. Application Data

(63) Continuation-in-part of application No. 10/190,638, filed on Jul. 9, 2002, now Pat. No. 6,916,294.

(51) Int. Cl.
*A61B 5/117* (2006.01)
*A61B 5/103* (2006.01)

(52) U.S. Cl. .................................. 600/587
(58) Field of Classification Search ............... 600/587, 600/547, 372, 300, 544, 504, 202, 206, 207, 600/229, 473; 606/1
See application file for complete search history.

(56) References Cited

U.S. PATENT DOCUMENTS

| | | | |
|---|---|---|---|
| 3,882,855 A | 5/1975 | Schulte et al. |
| 3,888,117 A | 6/1975 | Lewis |
| 3,958,562 A | 5/1976 | Hakim et al. |
| 4,147,161 A | 4/1979 | Ikebe et al. |
| 4,263,900 A | 4/1981 | Nicholson |
| 4,317,452 A | 3/1982 | Russo et al. |
| 4,735,208 A | 4/1988 | Wyler et al. |
| 4,784,150 A | 11/1988 | Voorhies et al. |
| 4,869,255 A | 9/1989 | Putz |
| 4,903,702 A | 2/1990 | Putz |
| 4,945,896 A | 8/1990 | Gade |
| 5,112,347 A | 5/1992 | Taheri |
| 5,201,325 A | 4/1993 | McEwen et al. |
| 5,207,227 A | 5/1993 | Powers |
| 5,247,932 A | 9/1993 | Chung et al. |

(Continued)

FOREIGN PATENT DOCUMENTS

DE   100 04 514 C 1   2/2000

(Continued)

OTHER PUBLICATIONS

Behrens et al., "Subdural and Depth Electrodes in the Presurgical Evaluation of Epilepsy" Acta Neurochir (1994) 128:84-87.

(Continued)

*Primary Examiner*—Max F. Hindenburg
*Assistant Examiner*—Brian Szmal
(74) *Attorney, Agent, or Firm*—DLA Piper US LLP

(57) ABSTRACT

An electrode device is disclosed comprising a deformable envelope, further comprising recording electrodes and a pressure recording port. The device allows for monitoring of brain retraction pressure and local cortical electrical activity including DC potential, as well as redistribution of the force applied during retraction and cushioning of the rigid edges of the brain retractor, thereby diminishing the chance of focal brain injury during surgery. Retraction pressure recorded is equal over the full area of contact. A means is disclosed for optional evacuation of air from the system to improve accuracy and fidelity of the pressure measurements. Local brain hypothermia may be induced via the bladder and attached catheter, thereby providing additional neuroprotection during brain retraction. The device also allows for measurement of intracranial pressure, DC potential, EEG and, optionally, other physiologic parameters in epileptic and severe head trauma patients for management of edema and injury.

62 Claims, 14 Drawing Sheets

U.S. PATENT DOCUMENTS

| | | | |
|---|---|---|---|
| 5,377,675 | A | 1/1995 | Ruskewicz et al. |
| 5,551,439 | A | 9/1996 | Hickey |
| 5,709,646 | A | 1/1998 | Lange |
| 5,769,781 | A | 6/1998 | Chappuis |
| 5,876,577 | A | 3/1999 | McAleer et al. |
| 5,916,171 | A | 6/1999 | Mayevsky |
| 5,997,484 | A | 12/1999 | Sugahara |
| 6,061,593 | A | 5/2000 | Fischell et al. |
| 6,093,145 | A | 7/2000 | Vom Berg et al. |
| 6,104,941 | A | 8/2000 | Huey et al. |
| 6,144,866 | A | 11/2000 | Miesel et al. |
| 6,296,615 | B1 | 10/2001 | Brockway et al. |
| 6,699,269 | B1 | 3/2004 | Khanna |
| 6,733,442 | B1 | 5/2004 | Larnard |

FOREIGN PATENT DOCUMENTS

| | | |
|---|---|---|
| JP | 09-327441-1 | 12/1997 |

OTHER PUBLICATIONS

Palatinksky et al., "SSEP and BAEP Monitoring of Temporary Clip Application and Induced Hypotension during Cerebrovascular Surgery" in Intraoperative Monitoring Techniques in Neurosurgery, (C.M. Loftus et al., eds.), 1994, Cpt. 7, pp. 61-71, McGraw-Hill, Inc., NY.

Rampil I.J., "Electroencephlogram" in Textbook of Neuroanesthesia with Neurosurgical and Neuroscience Perspectives, (M.S. Albin, ed.), 1996, Cpt. 6, pp. 193, 207-208, McGraw-Hill, Inc., NY.

Hongo et al., "Monitoring Retraction Pressure on the Brain," J. Neurosurg., vol. 66, Feb. 1987, pp. 270-275.

Donaghy et al., "Pressure Measurement Beneath Retractors for Protection of Delicate Tissues," American Journal of Surgery, 1972, 123:429-431.

Andrews et al., "A Review of the Brain Retraction and Recommendations for Minimizing Intraoperative Brain Injury," Neurosurgery, vol. 22, No. 6, Dec. 1993, pp. 1052-1063.

Piper et al., "The Camino Intracranial Sensor: Is it Optimal Technology? An Internal Audit With a Review of Current Intracranial Pressure Monitoring Technologies," Neurosurgery, 2001, 49:1158-65.

Rosenorn, J, "Self-Retaining Brain Retractor Pressure During Intracranial Procedures," Acta Neurochirurgica, 1987, 85:17-22.

Apan, A., "A Sensitive Brain Retractor for Neurosurgery," Neurosurg Rev., 1999, 22:230.

Aesculap—Spiegelberg, "Accuracy. Reliability. Peace of Mind. ICP and CPP Monitoring," BBraun.

Connolly, et al., "Hypothermic Cardiac Standstill for Cerrebral Aneurysm Surgery," Current Management of Cerebral Aneurysms, Part II: Techniques of Aneurysm Occlusion, vol. 9 No. 4, Oct. 1998, pp. 681-695.

BRAIN RETRACTION SENSOR

This application is a Continuation-In-Part of U.S. application Ser. No. 10/190,638, filed Jul. 9, 2002 now U.S. Pat. No. 6,916,294, the entire contents of which is incorporated herein by reference.

BACKGROUND OF THE INVENTION

1. Field of the Invention

This invention is related generally to intracranial sensors for prevention of retractor blade injury (i.e., "retraction injury") of the brain, and subdural monitoring devices.

2. Background

A retractor is an instrument used during surgery for, among other things, holding back structures adjacent to the immediate operative field (See, e.g., U.S. Pat. No. 5,769,781). During neurosurgical operations for aneurysms, tumors or other lesions located in the skull base, the surgeon must employ retracting devices in order to displace one or more lobes of the brain enough to gain adequate surgical exposure to the lesion. These retractors are adjusted by hand to optimize exposure. Unfortunately, it is very difficult for the surgeon to accurately gauge the amount of pressure actually applied to the brain during such placement of the retractor (see, e.g., Hongo et al., J Neurosurg 1987; 66:270–275). Moreover, it is also possible to inadvertently position the blade of the retractor such that a focal pressure point occurs at one particular area of the retractor blade pressing against the brain. Thus, injury to the brain can occur as a result of brain retraction when either the force applied is excessive or when the pressure is not adequately distributed to a large enough area of brain. This injury is thought to be the result of ischemia (inadequate blood flow) caused by the retraction, local trauma, or a combination of both.

It has been estimated that brain retraction injury occurs in approximately 10% of major cranial base tumor procedures and 5% of intracranial aneurysm surgeries (Andrews et al., Neurosurgery 1993; 33:1052–64). Various attempts have been made to develop technology to help minimize the incidence of this type of injury, with limited success. For example, a strain gauge or gauges attached to the retractor blade has been employed (Hongo et al., 1987; Rosenorn J., Acta Neurochir (Wein) 1987; 85:17–22). This approach has limited utility because pressure can only be measured from the point or points where the strain gauges are situated. As mentioned above, sometimes the brunt of the force occurs at the tip of the retractor blade where no strain gauge is present. Certainly this technique does little, if anything, to distribute force on the brain more evenly.

While knowing the amount of pressure applied will be helpful to the surgeon, the brain may be more or less sensitive to a given amount of pressure depending on its physiological state. The variables that influence the vulnerability of the brain to different degrees of retraction include the presence of subarachnoid hemorrhage (e.g., secondary to a ruptured aneurysm), depth of anesthesia, systemic parameters such as blood oxygen and carbon dioxide levels, and the particular region of the brain being retracted. As a result, electrophysiological monitoring of the brain can give a more accurate indication of when the threshold for injury is being approached. Intraoperative neurophysiological monitoring is commonplace during such operations, and typically the electroencephalogram (EEG) and somatosensory evoked potentials (SSEP) are employed. The electrodes commonly used are stainless steel. However, these modalities depend on the placement of electrodes on the scalp. Because of this, electrodes can only be placed to the extent that they do not interfere with the sterile surgical field, and obviously cannot be placed in the area of the craniotomy. Of course, this is precisely the part of the brain that needs to be monitored.

Thus, this type of recording from scalp leads can, at best, give information regarding regions of the brain adjacent to where the operation is occurring. Unfortunately, this method often reports erroneously favorable information that does not reflect the injury developing at the retractor site.

In neurosurgical operations where ischemia is anticipated (which includes most aneurysm procedures), high doses of anesthetics are typically administered to the patient to reduce cerebral metabolic rate and increase the tolerance of the brain to ischemia. Such high doses cause suppression of both the EEG and SSEP, thus rendering them ineffective for the detection of imminent brain injury. The recording of cortical direct current (DC) potentials from the brain is a technique that provides invaluable information about the functional status of the brain during situations of compromised blood flow (Ayad, doctoral dissertation ©1994; Sakaki et al., J Neurosurg 2001; 95:495–9). Further, DC potentials are not significantly affected by anesthetic agents. This technique was utilized experimentally in the 1950's during operations for epilepsy. However, with the exception of the clinical study currently investigating the device described herein, the benefits of DC potential for monitoring brain injury intraoperatively have not been put to use. This is, no doubt, because a practical method for applying the electrodes to relevant parts of the brain without obscuring the operative field has not been available.

Measuring such DC potentials requires the placement of a non-polarizable electrode (e.g., platinum or Ag—AgCl rather than stainless steel) on the cortical surface. Stainless steel and other electrodes cause artifactual potentials which prevent registration of the true voltage signal. The cortical electrode is referenced against a non-polarizable electrode placed at a remote site from the brain, and a high-input impedance DC amplifier is used to record the voltage. An extracerebral site is essential for the reference electrode in order for it to remain "indifferent" to injurious processes that may be occurring in the brain. Depolarizations (i.e., negative potentials) of greater than 4–5 mV typically develop when the brain is subjected to ischemia or trauma. DC potential is ideal for assessing the status of a small, localized area of the brain without penetrating its surface. Further, conventional EEG and SSEP recordings from platinum electrodes produce less noise than stainless steel electrodes during ischemia.

Strips of silicone rubber containing metal (e.g., Pt, stainless steel, etc.) electrodes known as "subdural grids" are commonly placed on the brain underneath the dura mater of certain patients with epilepsy for long-term recording of EEG to localize areas of seizure activity prior to surgery (e.g., U.S. Pat. No. 4,735,208). These materials are biocompatible, and have been tolerated very well for periods of up to several weeks when used for this purpose (Behrens E, Zentner J, et al. Subdural and depth electrodes in the presurgical evaluation of epilepsy. Acta Neurochir 1994; 128:84–87). However, such devices do not allow for monitoring of intracranial pressure. This latter capability would be helpful because many epileptics who have implanted grids develop local brain swelling, and recognizing a pressure increase would allow appropriate management of edema. Additionally, such a device, which also monitors intracranial pressure, may allow for concurrent measurement of such pressure and EEG postoperatively from severe head trauma patients who have undergone surgery for the management of said trauma.

Currently, there is no technology available to record electrical activity from areas of the brain that are being retracted. Instead, areas remote to the retraction site are monitored, providing sub-optimal and sometimes misleading information about the status of the brain. Two prior patents (U.S. Pat. Nos. 4,784,150 and 4,945,896) have incorporated technology to monitor local cerebral blood flow and metabolic parameters, respectively, into a brain retractor blade. Neither are equipped with a means for monitoring retraction pressure. Moreover, for the reasons discussed previously, local electrocortical activity provides a more readily interpretable index, compared to these measures, of when the threshold for injury is being reached.

With respect to monitoring retraction pressure, devices have been manufactured commercially in the past to perform this, however none are readily available at present (e.g., Codman CPM-100 Brain Retraction Pressure Monitor [Codman & Shurtleff, Inc. 15 Randolph, Mass.]; also see Hongo et al., 1987). Furthermore, such devices require proprietary accessory equipment that is expensive, and they are cumbersome to use (Andrews et al., 1993). Other devices are attached to the arm of the retractor blade rather than to the blade (McEwen et al., U.S. Pat. No. 5,201,325), and only convey information about the point of greatest pressure. Even where the "pressure responsive" surgical tool assembly is attached to the retractor blade (e.g. Nicholson, U.S. Pat. No. 4,263,900 and Lewis, U.S. Pat. No. 3,888,117), such devices do not permit recording of electrical activity.

The Codman CPM-100 device and the retraction pressure monitor of Nicholson (see also Donaghy et al., Am J Surg (1972) 123:429–31) all differ from the sensor of the present invention in other important structural respects. Retraction pressure monitors of Codman, Nicholson and Donaghy et al. employ an expandable reservoir with internal electrodes (i.e., the electrodes do not contact the underlying tissue). Air or other fluid is pumped into or out of the reservoir depending on electrical contact, resulting in inflation or deflation of the reservoir. Since air is one of the fluids utilized, there is no means for eliminating air from the system. Physiological saline cannot be used, as it would short-circuit the electrodes. Further, using air in these devices would not be compatible with conventional hydraulic pressure monitoring systems, and as such, any air-fluid interface would attenuate the fidelity and accuracy of the latter systems.

In contrast, the device described herein utilizes a flexible but relatively non-expandable bladder that can be, optionally, liquid-filled and free of air prior to use. This serves as an efficient mechanism to evenly distribute applied force throughout the entire area of contact. Alternatively, the device can be filled solely with air and free of liquid. The advantage of this type of system is that there is no hydraulic pressure exerted by a liquid column in the tubing which must be zeroed out during calibration (e.g. Bobo et al., U.S. Pat. No. 6,673,022). However, the disadvantage of employing air is that a somewhat expensive, specially designed measurement apparatus is required in order to measure the pressure within the bladder (e.g., Spiegelberg ICP monitor, [Aesculap, Inc., Center Valley, Pa., 2001]). The presently disclosed device provides an accurate means for measuring retraction pressure without the need for a fluid pump or internal electrodes.

In order to increase the tolerance of the brain to possible injury, various methods of neuroprotection may be employed during neurosurgical procedures such as the use of high doses of anesthetics, as discussed earlier. One of the most effective neuroprotectants is hypothermia, but there are limitations which prevent it from being used on a routine basis (see Connolly et al., Neurosurgery Clinics of North America (1998) 9(4):681–695). For example, generalized hypothermia to lower than 30° C. results in frequent cardiac arrhythmias and decreased blood clotting which may complicate surgery. Further, induction of deep hypothermia requires cardiopulmonary bypass, which is an involved procedure with risk of significant morbidity. On the other hand, local brain hypothermia may be equally effective as a neuroprotectant but does not suffer from the limitations of generalized hypothermia (see Ayad, doctoral dissertation ©1994). The device presently described provides a mechanism for induction of local brain hypothermia by instilling cooled liquid into the bladder via the double-lumen catheter.

There have been attempts to fabricate brain retractor blades which more favorably distribute pressure, so as to lessen the chance of injury (Vom Berg, U.S. Pat. No. 6,093,145 and Borsody, U.S. Pat. App. No. 2002/0022770). Neither are capable of monitoring retraction pressure or any other sensing modalities.

A second utility of the present invention pertains to its intracranial placement at the time of surgery for the purpose of postoperative monitoring of intracranial pressure (ICP), as well as the modalities of electrical activity described previously (i.e., as a subdural sensor). This information will permit the neurosurgeon and critical care physician to optimally manage brain swelling and injury after surgery.

There are two types of operations in which use of the subdural sensor (SS) may be indicated. The first was mentioned above, i.e., patients with intractable epilepsy that is refractory to anticonvulsant medication may undergo placement of many subdural electrode grids in order to localize the focus identified by the EEG monitoring. Because the placement of many grids involves some manipulation of surface of the brain, sometimes patients can develop significant brain swelling which results in abnormally raised ICP. Occasionally ICP is raised to the point that alteration of mental status occurs, and this may only be identified as such after the patient undergoes a CT scan of the head. By having a monitor of ICP in these patients, elevations in ICP can be identified sooner, and treated promptly with mannitol or steroids.

The second type of operation in which subdural placement of the device may be helpful is for severe closed head injury. In cases of cerebral contusion, massive swelling of the brain often occurs and if not treated appropriately, can result in coma or death of the patient. When severe swelling has occurred or is anticipated, often these patients are taken to the operating room to undergo removal of the damaged portions of the brain in order to provide room for the swollen brain and reduce ICP. Virtually all of these patients have some type of ICP monitor placed at the time of surgery to permit assessment of the swelling postoperatively. Currently there are two types of ICP monitors commonly used in this setting. The first is a ventriculostomy, which is an open-tipped catheter placed into the lateral ventricle of the brain and connected to a hydraulic transducer substantially similar to that used for the invention described. A ventriculostomy is advantageous because it permits not only measurement of pressure but also drainage of cerebrospinal fluid from the brain, which can aid in the lowering of ICP. However, after severe closed head injury, often the brain is so swollen that the ventricles are collapsed and placement of a ventriculostomy is impossible. The second type of ICP monitor currently available is an intraparenchymal probe which is placed into the substance of the brain through a small burr hole, and which records pressure from its tip by one of many methods (e.g., Camino fiberoptic monitor, Camino Laboratories, San Diego, Calif.). The disadvantages of this technique are that (1) it requires penetration of the brain with the probe, which itself causes a small amount of trauma, and (2) the pressure recorded from this type of probe is prone to non-trivial drift over a matter of days (Piper at al., Neurosurgery 2001; 49:1158–65). Furthermore, neither of these two types of ICP monitors permits the recording of local EEG or DC potential, which are valuable adjuncts in the assessment of brain injury. For these reasons, the present invention will be a superior monitoring device compared to the existing ICP monitors.

The tissue monitor described by Mayesvsky (U.S. Pat. No. 5,916,171) comprises a multiparametric apparatus able to monitor several modalities, including DC potential, ICP, a single channel of EEG, blood flow and NADH fluoremetry. Despite these aggregated modalities, there are a number of shortcomings. All parameters are recorded from the same, small area of cortex. Thus, all information will be reported from a small region that may not represent the bulk of the surrounding tissue, particularly, for example, if the area beneath the sensor is traumatized during placement, which might easily occur. Because it requires extensive, specialized equipment to operate, this system is clearly intended for use in a focused, research setting and not for routine monitoring of neurotrauma or epilepsy patients in the ICU.

As with a ventriculostomy, it should be noted that the pressure transducer utilized with the present device should be kept at the level of the distal end of the sensor (e.g., scalp incision) by the nursing staff in order to record an accurate pressure. Raising the transducer, due to the fluid column, will result in an artifactually low ICP and conversely, lowering the transducer below the appropriate level will cause an erroneously high ICP to be read. This aspect of the device can be readily managed by attentive staff, and is easily offset by the convenience, low cost, reliability and ubiquity of the standard hydraulic pressure monitoring apparatus in the intensive care unit and operating room. Alternatively, as discussed earlier, the sensor can be filled with air alone and not be susceptible to this fluid-column effect, but in that case would require the use of a specialized pressure measurement system (Speigelberg, 2001).

Last, various procedures require postoperative evacuation of residual fluids, for example, following craniotomy (see Jackson et al., Surgery (1971) 70:578–9). In fact drainage of serosanguineous wound fluid or CSF from the subdural space often plays an important part in the postoperative managemant of patients with craniotomies, especially trauma. Typically, the placement of drainage devices (e.g., Jackson-Pratt drain, Allegiance Healthcare, McGaw Park, Ill.) is similar to that for subdural grids. Consequently, many of the patients who would be candidates for placement of the subdural sensor would ordinarily have J-P drains placed at the time of surgery. Thus, a subdural sensor comprising a means to drain residual fluids would be a useful device.

The present invention as disclosed provides the desired capabilities absent in the foregoing devices, in that it is designed to permit monitoring of brain retraction pressure or ICP, as well as local cortical electrical activity, including DC potential (i.e., via multiple electrode sites). It permits registration of equilibrated pressure over the full length of contact of the retractor blade. Further, the present device as disclosed allows for redistribution of the forces applied to the brain during retraction so as to diminish the chance of focal brain injury during surgery. Protection of the brain from the rigid edges of the retractor blade is achieved without compromising visualization of the operative field. The induction of local brain hypothermia can be provided using the device for further neuroprotection during brain retraction. For use postoperatively, the instant device provides a closed system for egress of serosanguineous fluid into a sterile, external collector.

SUMMARY OF THE INVENTION

A device is disclosed comprising an inextensible pressure distribution means (e.g., elastomer grid) that allows for redistribution of pressure along the surface of the brain when said device is in contact with said organ. It is an object of this invention that when the device is applied to a retractor blade, such distribution of pressure can reduce retractor injury. It is another object of this invention that the device can be applied subdurally for pre- and post-operative evaluation of epileptic and traumatic brain injury patients.

In one embodiment, a brain retractor device is envisaged including a first end comprising a substantially inextensible first cavity, where the first end is integral with a retractor blade, a plurality of electrodes exposed along a first surface of the first end, a first electric conduit, a second conduit, which the second conduit allows for measuring pressure, and a second end comprising an exit port, which exit port engages the first and second conduit. Further, the second conduit may be hydraulic and may include a flexible, noncompliant material. Moreover, the second conduit may comprise one or more luminal surfaces and may further include a double lumen catheter, where the double lumen catheter engages separate fluid-flow directing connectors, such as but not limited to female luer-lock connectors.

In a related aspect, the electrodes are polarizable or non-polarizable, Further, where such electrodes are non-polarizable, a distal end of the first electric conduit and one end of a remote reference electrode electrically connect to a differential DC amplifier. In a further related aspect, the conduit exits from the sensor in a manner which minimizes deformity or pressure on the brain by the conduit itself.

In another related aspect, the device may include a retractor blade inlcuding a first aperture, where the first aperture allows the first and second conduits to traverse opposing blade surfaces. Further, a first end may comprise substantially flat, smooth atraumatic faces.

In one aspect, the first end comprises a thin, elastically deformable, bio-compatible material, where the bio-compatible material may include, but is not limited to, silicone-based materials, thermoplastic elastomer, low density polyethylene or polyurethane.

The device is envisaged to include an exposed outer surface of a first cavity which extends beyond the edges of the retractor blade, where the extended surface does not obscure the operative field.

Further, a device is envisaged, wherein the first cavity comprises a bladder or a network of interconnected lumens internal to the exposed surface. In a related aspect, the device is able to operate whether the first cavity is filled with a gas or a liquid.

In another related aspect, when the first cavity is filled with a liquid, the liquid is may include, but is not limited to, normal saline, buffered salt solution, Ringer's solution, Elliot's B solution, or mock cerebrospinal fluid. In a related aspect, the cavity includes a heat exchange fluid for induction of local brain hypothermia for the purpose of neuroprotection, where the fluid can be cooled by extracorporeal refrigeration.

Further, the fluid may be cooled to a temperature of as low as about 0° C. In one aspect, the fluid is cooled to between about 0° C. to about 10° C. In another related aspect, the heat exchange fluid may include, but is not limited to, saline, lactated Ringer's solution, water, Elliot's B solution or mock cerebrospinal fluid.

In one aspect, an electric conduit further includes a first tail distal to the first end, where the tail allows for communication between the device and at least one peripheral apparatus. Such a device may include, but is not limited to, at least one adjunctive monitoring modality.

In a related aspect, such a modality may measure physiological parameters including brain compliance or elastance, cerebral impedance, fluid flow, partial pressure of oxygen or carbon dioxide, temperature, pH, metabolites or a combination thereof, where the fluid flow may be blood flow. In a related aspect, the metabolites may include, but are not limited to, extracellular potassium or glutamate.

In another related aspect, the first cavity can accommodate pressures of between about one mm Hg and about 120 mm Hg.

In one aspect, a retractor blade having a substantially polygonal shape is envisaged, where the polygonal shape is substantially quadrilateral, further including rounded edges at straight-line boundaries. In another aspect, the retractor blade is tapered or blunt.

In one embodiment, a sub-dural device is envisaged including, a first end comprising a substantially inextensible cavity, a plurality of electrodes exposed along a first surface of the first end, a first electric conduit, a second conduit, which the second conduit allows for measuring pressure, and a second end comprising an exit port, which exit port engages the first and second conduit, where the device is able to operate whether the cavity is filled with a gas or a liquid.

It is an object of this device, when applied subdurally, that egress of subdural wound fluid may be directed through a third lumen of a conduit into an external collection device, such as a bag. In a related aspect, the fluid is allowed to flow into such an external collection device by gravity flow.

It is an object of this invention that hydraulic pressure, equilibrated throughout the distribution means, can be recorded from the catheter by a standard strain gauge apparatus used in the clinical setting. This equilibrated pressure represents brain retraction pressure when the device is situated between the brain and retractor blade. When situated in the subdural space, the equilibrated pressure reflects ICP. For example, see method as disclosed in Ikebe et al. (U.S. Pat. No. 4,147,161).

It is an object of the present device to comprise a process of redistribution of the forces applied to the brain during retraction so as to diminish the chance of focal brain injury during surgery. Moreover, the process further comprises monitoring of brain retraction pressure and local cortical electrical activity, including but not limited to DC potential, EEG and evoked potentials. In a related aspect, the surgeon practicing such monitoring adjusts retraction based on abnormal readings correlating with retraction pressure and cortical electrical activity. In a further related aspect, such abnormal recordings include but are not limited to, loss of EEG fast activity accompanied by slow waves, burst suppression EEG patterns, EEG suppression, suppression of evoked potential amplitude, evoked potential latency delay or negative DC potential shift. For example, when the negative DC potential shift is >3 mV, this would be considered an abnormal reading.

It is an object of the present device to comprise a process of concurrent measurement of intracranial pressure and local electrical activity (previous paragraph) postoperatively from severe head trauma patients who have undergone surgery for the management of said trauma.

It is an object of the present device to comprise a process of local brain hypothermia for the purpose of neuroprotection during brain retraction.

It is a further object of the present device to comprise a process of monitoring epileptics who have implanted grids to determine the degree of local brain swelling for appropriate management of edema.

These and other important objects will be apparent from the descriptions of the instant invention which follow.

DETAILED DESCRIPTION OF THE INVENTION

Definitions

Figure 1:
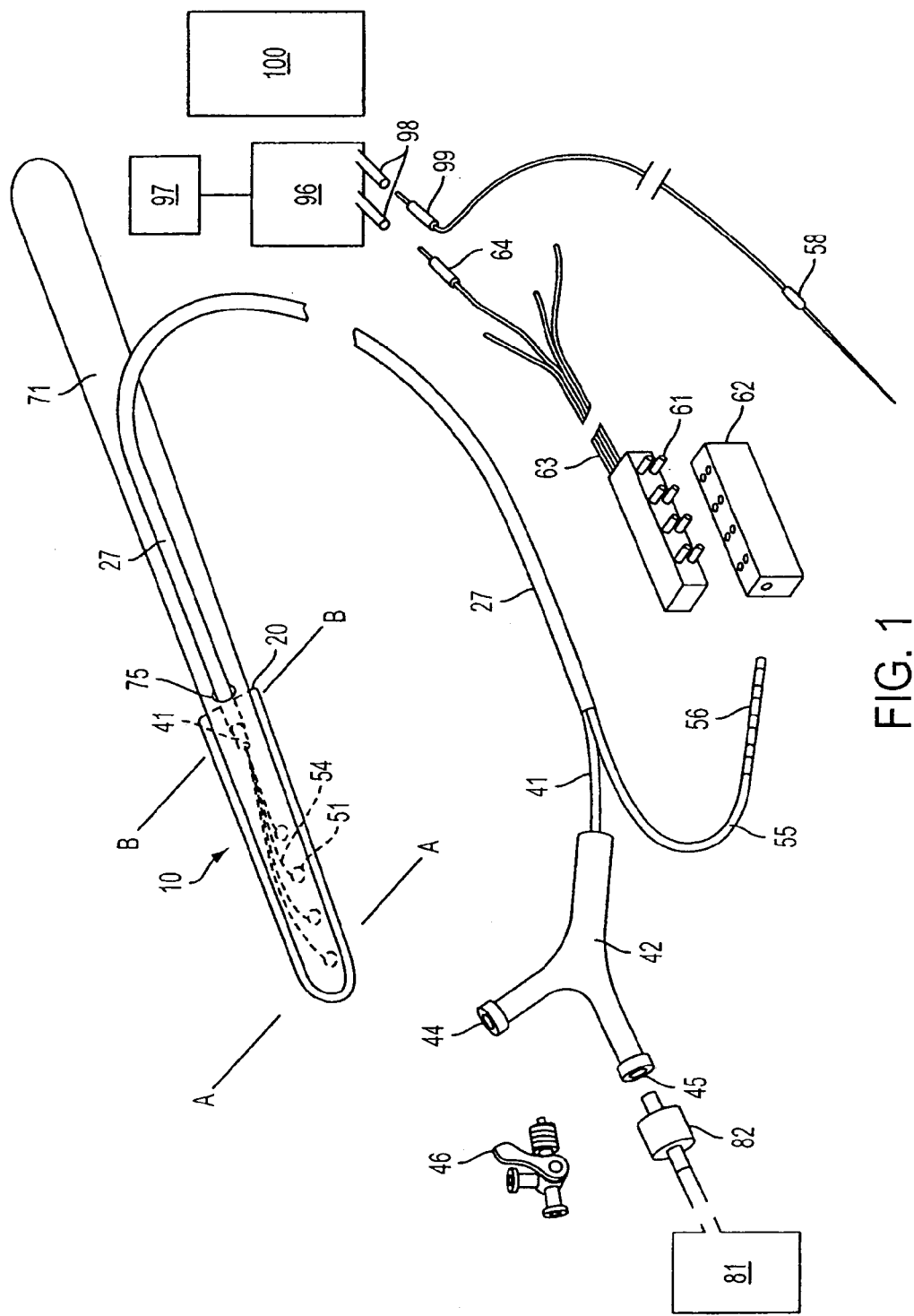
FIG. 1 Enlarged perspective view of one embodiment of brain retraction sensor (BRS) including proximal ends of electrode tail and double-lumen catheter. Also illustrated is a proprietary EEG cable assembly and connection (via stopcock) to hydraulic pressure recording apparatus.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention.

As used herein "subdural", including grammatical variations thereof, means situated underneath the dura mater and overlying the pia mater or arachnoid membrane of the brain.

As used herein "sensor", including grammatical variations thereof, means a device designed to respond to physical stimuli such as, but not limited to, electrical, temperature, blood flow, or partial pressure of oxygen or carbon dioxide, and transmit resulting impulses for interpretation, recording, movement or operating control.

As used herein, "adjunctive monitoring modality", including grammatical variations thereof, means a device for observing a biological condition or function joined or added to the retractor device but is not essentially a part of it, where said device for observing serves usually as a physical diagnostic/therapeutic agency. For example, a device that is electrically coupled to the retractor, where the device measures $O_2$ partial pressure is such an adjunctive monitoring modality.

As used herein, "substantially polygonal shape", including grammatical variations thereof, means a closed plane figure bounded by straight lines.

As used herein, "substantially quadrilateral shape", including grammatical variations thereof, means a polygon of four sides.

As used herein "substantially inextensible cavity", including grammatical variations thereof, means a fixed or defined limit of expansion of an unfilled space within a mass. In a one embodiment, the cavity has a capacity of expansion of between about 5% and about 10% volume change from pre-filled resting state (e.g., liquid filled without force applied) per 100 mm Hg change in pressure. In another embodiment, the cavity has a capacity of expansion to include but not limited to about 6%, 7%, 8% or 9% volume change from pre-filled resting state per 100 mm Hg change in pressure. In a related aspect, the cavity would occupy a confined space of between about 0.3 mm$^3$ and about 1.2 mm$^3$ in the liquid-filled, expanded state. In a further related aspect, the cavity would occupy a confined space of, but not limited to, about 0.4 mm$^3$, 0.5 mm$^3$, 0.6 mm$^3$, 0.7 mm$^3$, 0.8 mm$^3$, 0.9 mm$^3$, 1.0 mm$^3$, or 1.1 mm$^3$ in the liquid filled, expanded state.

In another related aspect, a distribution means or elastomer grid comprising the first elongated end contains an unfilled space which includes but is not limited to a cavity, bladder, sinus, dilation, hollow or interconnected lumen, wherein the surfaces of such distribution means are minimally elastically deformable, essentially allowing for a low amount of variation in volume, and where such means remains substantially flat when such space is filled.

As used herein "cistern", including grammatical variations thereof, means a reservoir for liquids.

As used herein "configured", including grammatical variations thereof, means designed to fit a particular space. In one embodiment, the dimensions of the instant device are such that length and width of the distribution means are between about 5 cm to about 10 cm (length) and about 2 cm to about 3 cm (width), respectively. In a related aspect, the length is contemplated to be about 6 cm or 7 cm and the width is contemplated to be about 2.1 cm, 2.1 cm, 2.3 cm, 2.4 cm, 2.5 cm, 2.6 cm, 2.7 cm, 2.8 cm, or 2.9 cm. In a further related aspect, the subdural sensor the length of the distribution means is between about 13 cm to about 15 cm, including the drain tip.

As used herein "substantially flat" or "relatively thin", including grammatical variations thereof, relate to a range of thickness of the BRS/SS devices corresponding to be between about 1 mm and about 4 mm. In one embodiment, the thickness of the instant device is between about 1 mm to about 1.5 mm in the collapsed state and between about 2.5 mm to about 4.0 mm in the fully expanded state. In a related aspect, the thickness of the device is about 1.1 mm, 1.2 mm, 1.3 mm or 1.4 mm in the collapsed state, and about 2.6 mm, 2.7 mm, 2.8 mm, 2.9 mm, 3.0 mm, 2.1 mm, 3.2 mm, 3.3 mm, 3.4 mm, 3.5 mm, 3.6 mm, 3.7 mm, 3.8 mm or 3.9 mm in the fully expanded state.

As used herein "labyrinthine network", including grammatical variations thereof, means an array of elements (to include but not limited cavities, bladders, sinuses, dilations, hollows or interconnected lumens) combined to form an substantially inextensible cistern within the distribution means of the instant BRS/SS.

As used herein "matrix", including grammatical variations thereof, means material in which something is enclosed or embedded.

As used herein "integral", including grammatical variations thereof, means formed as a unit with another part. For example, a cavity that is affixed to a retractor blade is integral with said blade.

As used herein "fluid-flow directing connectors", including grammatical variations thereof, means a coupling which guides the route of fluid movement.

As used herein, "heat exchange fluid", including grammatical variations thereof, means a material (i.e., liquid, gas or fluent solid), which transfers thermal energy from one contact area to another.

As used herein, "local hypothermia", including grammatical variations thereof, means a method of cooling a localized area of the brain without appreciably cooling remote areas of the body.

As used herein "conduit", including grammatical variations thereof, means a natural or artificial channel through which something is conveyed. In one embodiment, that which is conveyed is a fluid. In another embodiment, the fluid is a gas or physiologically inert liquid, such as saline.

As used herein "elastically deformable", including grammatical variations thereof, means an ability to become misshapen or to change size or shape while being able to recover size and shape after said change.

As used herein "bio-compatible", including grammatical variations thereof, means adaptability with living tissue or a living system by not being toxic or injurious and not causing immunological rejection. In a related aspect, bio-compatible materials include, but are not limited to, silicone-based materials, thermoplastic elastomers, low density polyethylene, polyurethane and other thermoplastic materials.

As used herein "noncompliant", including grammatical variations thereof, means unyielding to condition, treatment or operation. For example, a tube composed of stainless steel or hard plastic would be considered noncompliant.

As used herein "residual fluid", including grammatical variations thereof, means bodily fluids left behind after surgery or injury to the brain. For example, serosanguineous fluid.

As used herein "lumen", including grammatical variations thereof, means the cavity or bore of a tube.

As used herein "surface", including grammatical variations thereof, means the superficial aspect of something. For example, the superficial aspect of a cavity would be considered a surface.

As used herein "atraumatic", including grammatical variations thereof, means without injury to living tissue, where such injury would typically be caused by an external agent.

As used herein "fluid", including grammatical variations thereof, means a substance having either the qualities of a liquid or a gas.

As used herein "hydraulic", including grammatical variations thereof, means operated, moved, or effected by means of water, gas or other fluid in motion.

As used herein, "physiologically inert", including grammatical variations thereof, means a substance that does not affect a characteristic appropriate to normal organism functioning, wherein said substance lacks a chemical or biological effect.

As used herein, "biological fluid flow", including grammatical variations thereof, means blood flow and CSF (cerebral spinal fluid) flow.

As used herein "burr hole" means a perforation in the calvarium made by a surgeon for the purpose of placing a drain or other device, or for facilitating removal of a bone flap. The diameter of a typical burr hole is between about 1 cm and 1.5 cm.

As used herein "perforation", including grammatical variations thereof, means a hole made by or as if by piercing or boring.

As used herein "spatula", including grammatical variations thereof, means a malleable metal blade used to retract brain tissue. The term is interchangeable with "retractor blade".

As used herein "aperature" means a hole or pore in a structure through which something passes.

As used herein "gravity flow", including grammatical variations thereof, means the movement of a material that is either a fluid or a solid by the attraction of the mass of the earth.

DC amplifier as used herein means an amplifier with input impedance $>10^{12}$ $\Omega$, has an infinite time constant, which may be battery powered, but not so limited, and permits measurement of voltage potential between active and reference inputs, allowing amplification of signal for recording on a monitor.

Embodiments

The present invention envisages a device comprising a substantially inextensible, pressure distribution means contained within a mass. The mass comprises a thin, elastically deformable, biocompatible composition. In one embodiment, such a device, for example, is envisages to include a cavity which has a fixed or defined limit of expansion within said mass. Such a cavity may be actualized by a membranous sac or bladder. Alternatively, it may be actualized by a labyrinthine network of tubes or interconnected chambers within a matrix of compressible material where the totality of luminal volume is continuous with two exit ports.

In one embodiment, a cavity is integral with a retractor blade.

In a related aspect such a device allows for redistribution of pressure along the surface of an organ when said device is in contact with said organ. In one embodiment, the device is placed in contact with a brain. In another embodiment, the brain is a human brain.

The device of the present invention is envisaged to measure physiological responses, including but not limited to EEG, intracranial pressure, DC potential and evoked potentials. Other physiological responses which may be measured by the invention include but are not limited to local cerebral blood flow (e.g., Powers, U.S. Pat. No. 5,207,227) and oxygen partial pressure (e.g. McAleer et al., U.S. Pat. No. 5,876,577; also, Miesel et al., U.S. Pat. No. 6,144,866). In one embodiment, the device of the present invention concurrently measures physiological responses and focal pressure exerted on the brain when integral or releasably coupled to a tool which produces such focal pressure. In a related aspect, said tool includes, but is not limited to a brain retractor.

In one embodiment, the brain retraction sensor (BRS) described herein incorporates a subdural electrode grid and a double-lumen plastic catheter into a thin, silicone rubber envelope which can be filled, optionally, with sterile saline through the catheter. The second port of the catheter, optionally, allows air bubbles to be evacuated from the silicone 'bladder'. In one embodiment, electrodes are present on the exposed surface of the device when the cavity containing component is integral with the retractor blade. Once the bladder is filled with saline, a stopcock on the secondary port is closed and the primary port is connected to a conventional pressure-recording setup in the operating room, as is commonly used for measuring arterial or central venous blood pressure. In a related aspect, calibration of the device is carried out with the sensor held at the level of the brain region to be retracted. In another related aspect, a proprietary cable is attached to the 'tail' of the grid assemble so that each of the four metal electrodes can be individually connected to input leads of a recording monitor (e.g., see Putz, U.S. Pat. No. 4,869,255). In a further related aspect, a separate platinum needle electrode is inserted by the surgeon into temporalis, or other exposed muscle, so as to provide a reference for measuring DC potential.

In one embodiment, when the surgeon is prepared to begin brain retraction, the retractor blade (attached to a flexible steel arm) is positioned on the brain as it normally would be placed. The BRS contacts the portion of the brain being retracted. In a related aspect, the fluid-filled bladder distributes the applied retraction pressure equally over the whole surface of the sensor, thereby eliminating focal pressure points prone to cause injury. In a further related aspect, because the pressure within and along the sensor is equal, the measurement of retraction pressure transduced through the catheter is a more meaningful representation than merely pressure at only one particular point, since pressure may vary considerably along the retractor blade if no bladder is present.

In another embodiment, important information, supplemental to retraction pressure is obtained by recording EEG and/or DC potential from each of the four metal contacts. When deemed necessary, this information can be conveyed to the surgeon by the person monitoring the parameters, so that adjustments can be made in the retractor positioning and injury to the brain can be avoided.

As stated above, the present invention is also directed to intracranial placement of a subdural sensor at the time of surgery for the purpose of postoperative monitoring of intracranial pressure (ICP), thus, permitting the neurosurgeon and critical care physician to optimally manage brain swelling and injury after surgery. For example, in one embodiment, at the conclusion of surgery, the sensor is placed underneath the dura mater on the surface of the brain. Typically the bone flap (i.e., piece of calvarium removed during the operation) has 2 or more burr holes approximately ½" in diameter along its perimeter which facilitate the craniotomy at the beginning of the procedure. Thus, at the conclusion of the case, when the bone flap is replaced, the plastic catheter and electrode-tail of the sensor can be allowed to exit the skull via one of the burr holes and then exit the scalp through a small puncture site in the skin.

The technique for placement of the instant device described above (i.e., intracranial placement) is identical to that of a subdural Jackson-Pratt drain (Allegiance Healthcare, McGaw Park, Ill.) for postoperative evacuation of residual fluid following craniotomy (see Jackson et al., Surgery (1971) 70:578–9). As stated earlier, i.e., those who would be candidates for placement of the subdural sensor. Therefore, in another embodiment, the subdural sensor incorporates a drain (comparable to a J-P) into the distal end and catheter of the device in order to permit egress of subdural fluid into an external collection bag. In a similar fashion to J-P, the instant device can easily be removed at the bedside of a patient after placement whenever its use in no longer required (i.e., without requiring additional surgery).

DETAILED DESCRIPTION OF PREFERRED EMBODIMENTS

FIG. 1 illustrates a perspective view of a Brain Retractor Sensor (BRS) 10, representing various parts comprising a fully assembled device, including cross-sectional planes A and B.

The BRS 10, includes an elongated elastomer grid 20 fashioned into an enclosed bladder, which is attached to the malleable brain spatula 71.

The grid 20 further includes a number of flat platinum electrode disks 51 partially exposed and coplanar with the elastomer grid 20 on the tissue engaging, front face of grid 20, through which such electrodes make contact with said tissue. Also, internal to the grid 20 are lead wires 54, one wire 54 attached to each electrode 51. Lead wires 54, each of which has its own thin layer of insulation (e.g., but not limited to, Teflon®), come together and engage at one end of the grid 20 where they separately enter a conduit 27. Conduit 27 traverses an aperture 75 in the spatula 71 so as to reside on the opposite face of the spatula proximally, that is, the face opposite the brain.

In the embodiment illustrated in FIG. 1, the grid 20 further includes a substantially inextensible cavity or bladder. This grid 20 may comprise silicone-based materials, thermoplastic elastomers, low-density polyethylene, polyurethane and other thermoplastic materials. In one embodiment, the grid comprises Silastic®, a biocompatible, silicone rubber material available from Dow Corning.

The cavity or bladder meets at one end of the grid 20 and engages the conduit 27, where said conduit comprises one end of a hydraulic double lumen catheter 41, which engages said bladder at one end of grid 20, and one end of a separate electrical conduit 55, which engages the lead wires 54 at the same end of grid 20. The hydraulic double lumen catheter 41 allows for ingress and egress of fluids into and out of the bladder/cavity, e.g. air, saline, low temperature coolant, etc. The electrical conduit allows for communication of electrophysiological information between the contacted tissue and external apparatus (e.g., EEG monitor).

A second end of the hydraulic double lumen catheter 41 engages a housing 42 containing twin hydraulic connecting ports 44 and 45 (e.g., luer-locks), where one connecting port is separately attached to one lumen comprising the hydraulic double lumen 41.

Further, one of the twin hydraulic connectors 44 is used for the evacuation of air bubbles in the hydraulic conduit 41 through the stopcock 46. Moreover, the other member of the twin connectors 45 (i.e., for connecting to hydraulic pressure recording apparatus) is connected to a strain gauge apparatus 81 via a male luer-lock connector 82. Said gauge apparatus 81 comprises a conventional output display, monitor and suitable power source.

A second end of the electrical conduit 55 comprises a contact/connector for external apparatus such as an EEG device, where the tail comprises a cable assembly 56. The contacts on the cable assembly 56 engage the EEG cable assembly connecting block 62, where the block engages connecting wires 63 (which includes male EEG input pin jack 64) of the EEG cable assembly via connecting pins 61. Further, said input pin jack 64 electrically connects to a conventional EEG, where said EEG comprises a conventional-output display, monitor and suitable power source.

At least one of the connecting wires 63 of the EEG cable assembly electrically connects to a DC amplifier 96 at electrical connection 98. A platinum needle electrode 58 also electrically connects to the DC amplifier 96 and serves as a reference electrode. Said DC amplifier 96 comprises a conventional output display, monitor and suitable power source. Moreover, at least one of the connecting wires 63 of the EEG cable assembly electrically may connect to a separate external apparatus 100, wherein apparatus 100 comprises a conventional output display, monitor and suitable power source.

Such a set up allows for real-time monitoring of electrophysiological responses of the brain during retraction procedures.

Figure 2A:
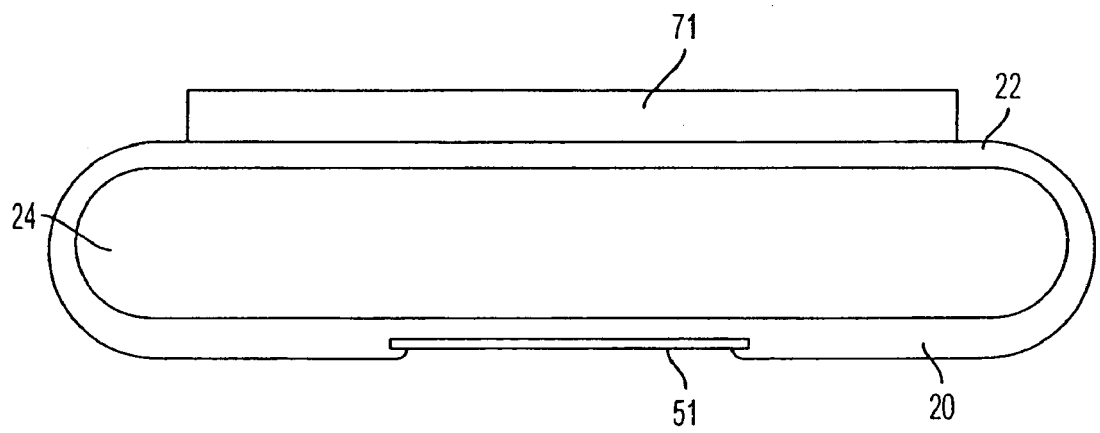
FIG. 2A Cross-sectional view of one embodiment of BRS at point A from FIG. 1 with retractor blade attached.

In FIG. 2A, a cross-sectional view of the BRS 10 is illustrated from the perspective from point A of FIG. 1.

A detailed view of the fluid-filled (expanded) bladder/cavity 24 is shown in FIG. 2A, including the roof 22 and the bladder/cavity 24 of the elastomer grid 20. Further, a partially exposed electrode 51 which makes contact with the tissue (i.e., the brain) is also shown.

Brain retractor blade 71 is shown attached to roof of bladder 22. Lateral edges of the bladder extend beyond the edges of the retractor blade to the extent that they cover the thickness of the blade when the silicone edges are flexed to as much as 90°.

Figure 2B:
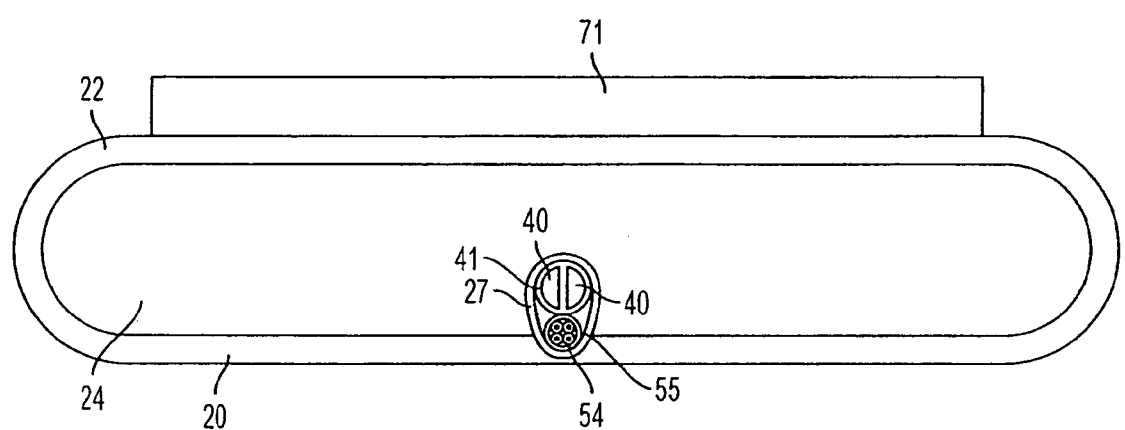
FIG. 2B Cross-sectional view of BRS at point B from FIG. 2.

In FIG. 2B, the cross-sectional view of the BRS 10 is illustrated from the perspective from point B of FIG. 1.

A detailed view of the fluid-filled (expanded) bladder/cavity 24 is shown in FIG. 2B, including the roof 22 and bladder/cavity 24 of the elastomer grid 20, as well as the retractor blade 71. Further, a cross-section of conduit 27, which sheathes the hydraulic double lumen catheter 41 and electrical conduit 55, is also shown.

Cross-sectional detail of the sheathing-conduit 27 illustrates the inner lumenal surfaces 40 of the double lumen catheter 41 and the electrical conduit 55, including the coated wire leads 54. The lumens each serve separate purposes; i.e., one lumen is for the evacuation of gases such that there are no air bubbles present in the conduit and cavity/bladder, and the other lumen to measure/monitor pressure.

Figure 3:
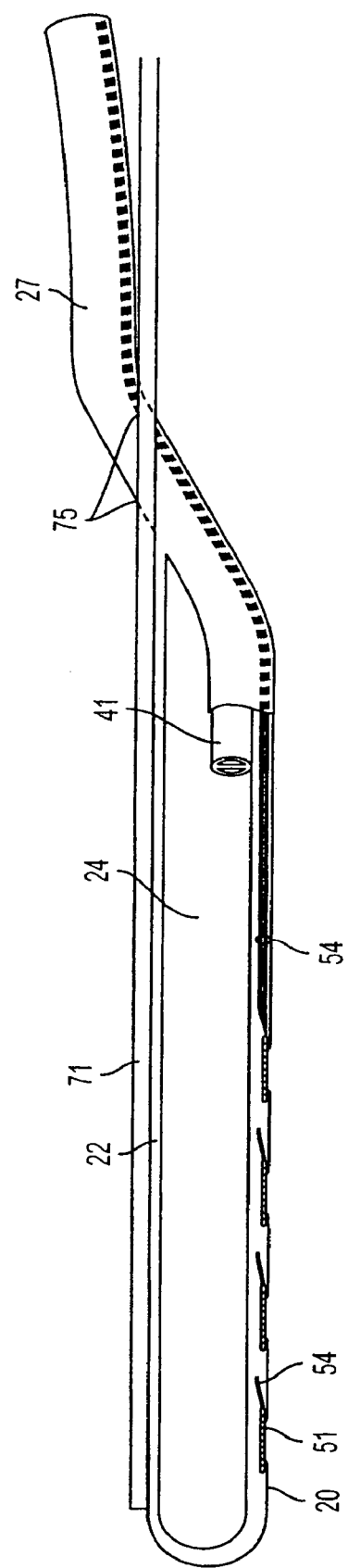
FIG. 3 Longitudinal section view of BRS at a point just adjacent to midline.

In FIG. 3, a longitudinal-section view just adjacent to the midline of the expanded BRS 10 is illustrated. This view shows four partially exposed electrodes 51, including their associated lead wires 54 coming together and engaging at one end of the grid 20. Further, the figure shows one end of the double lumen catheter 41 engaging the bladder/cavity 24. As both the lead wires 54 and double lumen catheter 41 extend away from the grid 20, they are sheathed in conduit 27.

FIG. 3 also shows the roof 22 of said cavity/bladder 24 adherent to the lower face of retractor blade 71. Conduit 27 is shown to traverse the blade via aperture 75 such that beyond this point, the conduit lies on the opposite face of the retractor blade.

Figure 4:
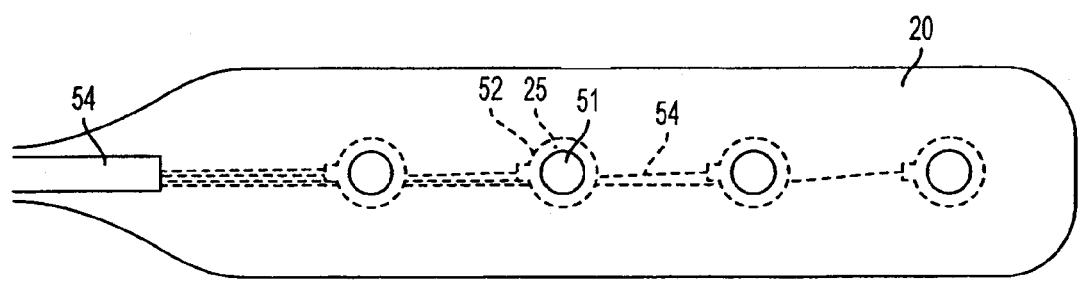
FIG. 4 Plane view of bottom (contact surface) of either BRS or subdural sensor (SS).

FIG. 4 illustrates a plane view of the bottom (tissue contact surface) of a retractor or subdural device.

The figure shows in detail four partially exposed electrodes 51, including a thin rim of Silastic® 25 in the bladder floor of the grid 20 overlying the outer margin of the Pt electrode 51 at 52, where the thin outer rim of Silastic® 25 holds the electrodes 51 in the grid 20. Further, as shown in the figure, each electrode 51 engages a separate coated lead wire 54, where the lead wires 54 come together at one end of the grid 20 at electrical conduit 55.

Figure 5:
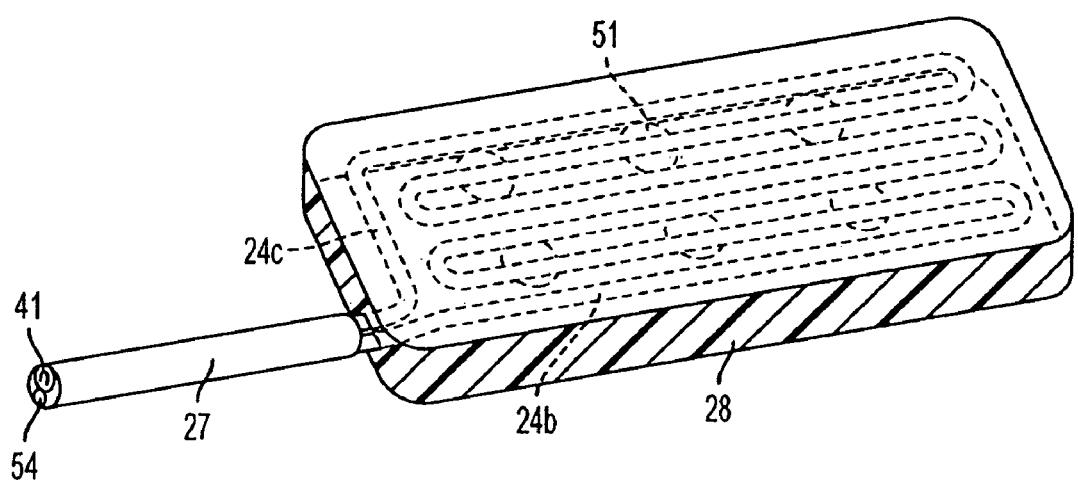
FIG. 5 Perspective view of alternative embodiment of distribution means for either BRS or intracranial sensor illustrating labyrinthine network of interconnected lumens continuous with both inlets of double-lumen conduit.

FIG. 5 is a perspective view of an alternate embodiment of the distribution means for either retractor application or subdural (intracranial) application.

In FIG. 5 the distribution means is illustrated by a series of interconnected lumens 24b and 24c. Each end of each lumen 24b and 24c is separately engaged to only one lumen of the double lumen catheter 41. Also shown are the electrodes 51 and the sheathing conduit 27, where the conduit 27 comprises the coated wire leads 54. Further, the figure also shows a compressible matrix cushion 28 which houses the lumens 24b and 24c, as well as the electrodes 51 and wire leads 54 (not shown within matrix).

Figure 6:
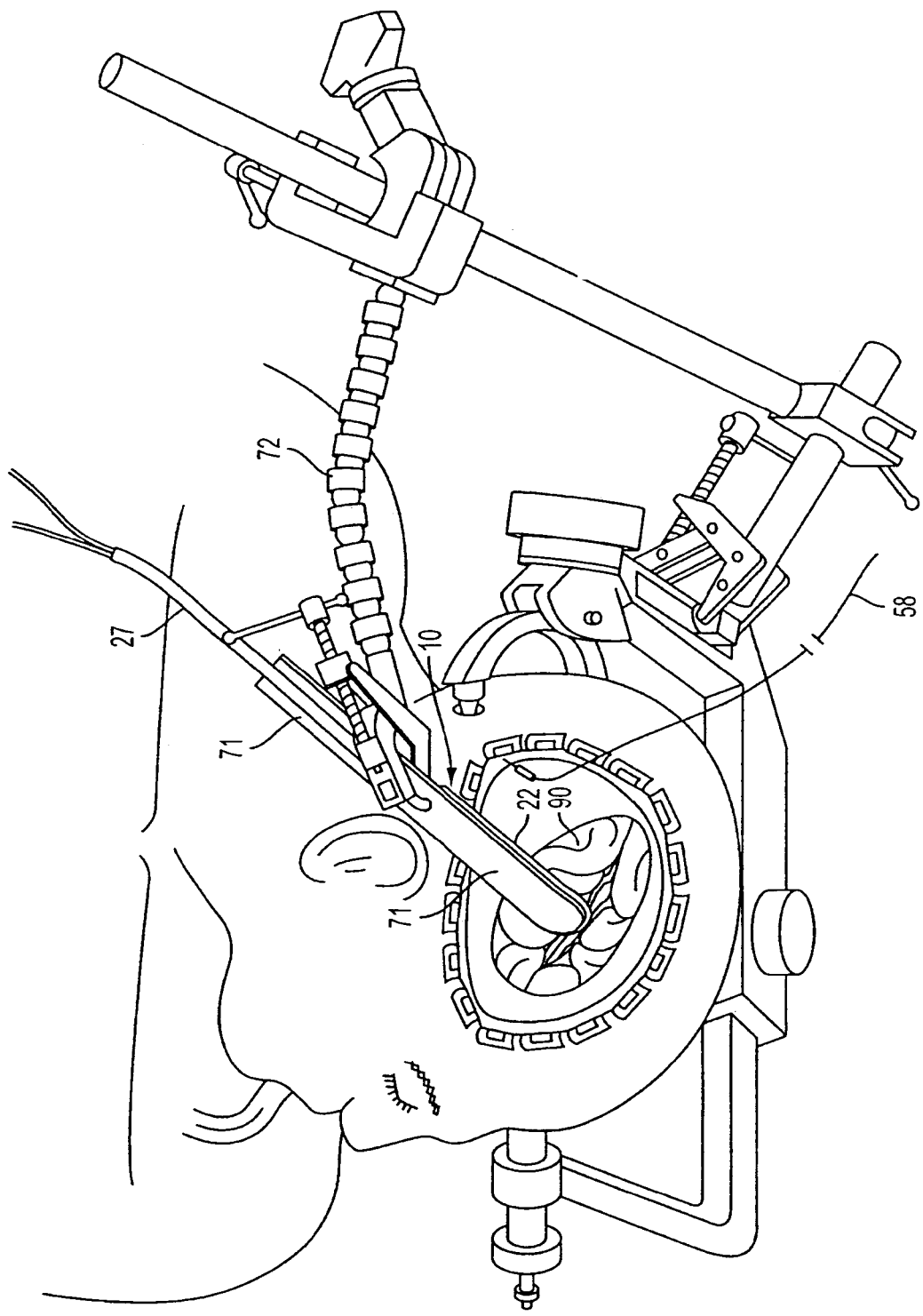
FIG. 6 Perspective view of BRS in use with a Greenberg retraction assembly for neurosurgical operation requiring retraction of patient's right temporal lobe.

FIG. 6 is a perspective view of the BRS 10 in use with a Greenberg retraction assembly 72 during retraction of a patient's right temporal lobe 90, includes a platinum needle reference electrode with male EEG input pin jack on distal end 58. The figure also shows a malleable metal brain retractor blade 71 with an integral BRS 10. The lateral edges of the roof of the bladder 22 extending beyond the retractor blade 71 are visible in the figure. Further, the sheathing conduit 27 is also shown.

Figure 7:
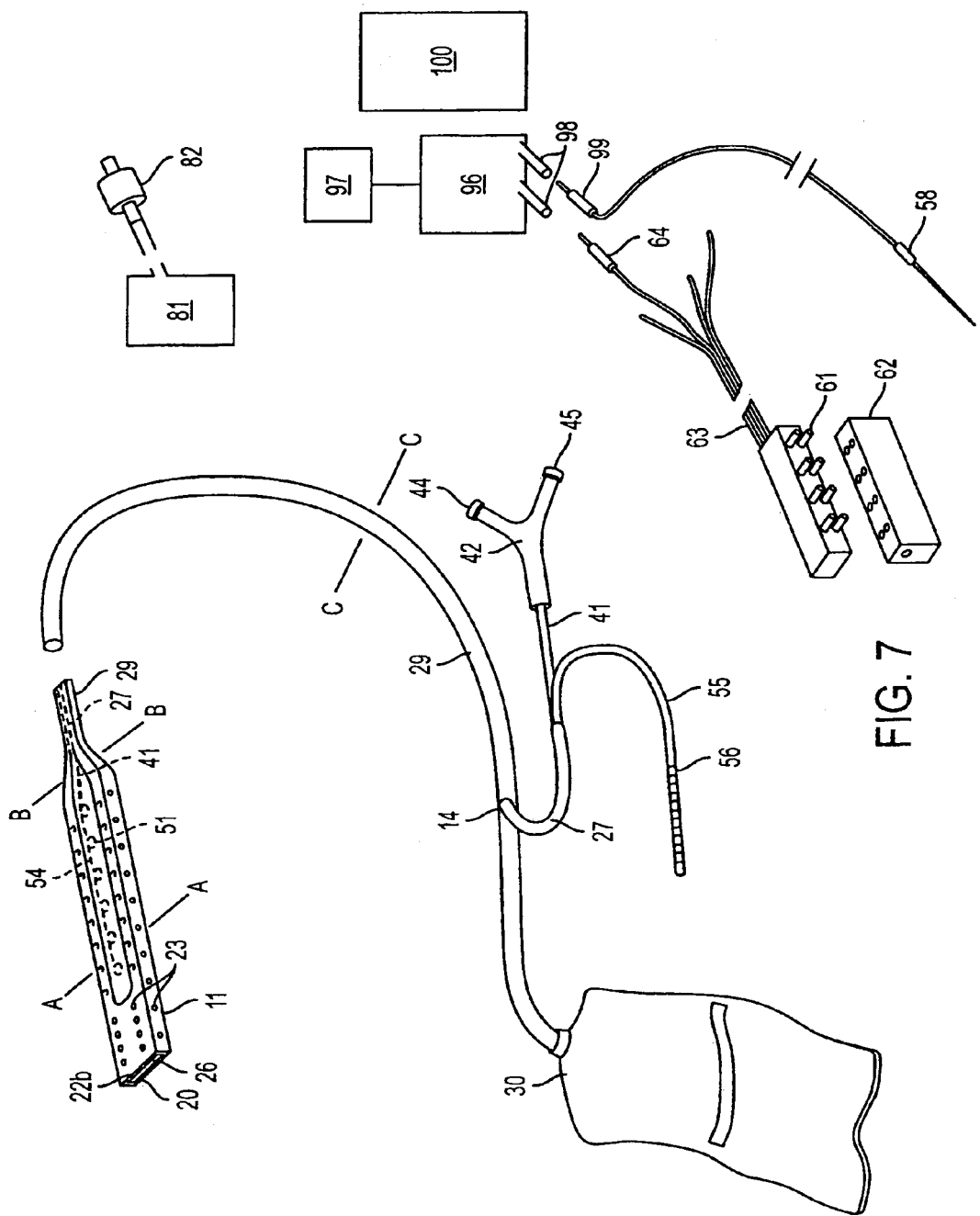
FIG. 7 Perspective view of one embodiment of the subdural sensor illustrating the perforated drain incorporated into the sensor. The exiting conduit includes a solid drainage tube, double-lumen catheter with luer-lock ports, and the electrode tail.

FIG. 7 illustrates a perspective view of a Subdural Sensor (SS) 12, representing various parts comprising a fully assembled device, including cross-sectional planes A, B and C.

The SS 12, includes an elongated elastomer grid 20. The grid 20 comprises a number of flat platinum electrode disks 51 partially exposed and coplanar with the elastomer grid 20 on the tissue engaging, front face of grid 20, through which such electrodes make contact with said tissue. Also, internal to the grid 20 are lead wires 54, one wire 54 attached to each electrode 51. Lead wires 54, each of which has its own thin layer of insulation (e.g., but not limited to, Teflon®), come together and engage at one end of the grid 20 where they enter a conduit 27. Moreover, conduit 27 is sheathed within the lumen of a second conduit 29.

In the embodiment illustrated in FIG. 7, the grid 20 further includes a subdural drain, the holes 23 of which are exposed on the outer surface of the grid 20, and where the roof of the drain is at 22b. Further, the grid 20 comprises a substantially inextensible cavity or bladder, where the roof of the cavity/bladder is continuous with roof 22b. The grid 20 may comprise silicone-based materials, thermoplastic elastomers, low-density polyethylene, polyurethane and other thermoplastic materials. In one embodiment, the grid comprises Silastic®, a biocompatible, silicone rubber material available from Dow Corning.

The subdural sensor also comprises a lumen 26, where the lumen 26 serves to evacuate residual fluids such as, for example, serosanguineous wound fluid or CSF. Such fluids collect in the lumen 26 and flow by gravity to a fluid collection bag 30 via the sheathing conduit 29. Further, said sheathing conduit 29 comprises a sealed exit port 14 for emergence of the conduit 27 from the sheathing conduit 29. Moreover, said exit port 14 may be sealed by any means known in the art (e.g., but not limited to, a gasket), such that residual fluid collected from the lumen 26 of the subdural drain does not leak from said exit port 14.

The cavity or bladder meets at one end of the grid 20 and engages the conduit 27. Conduit 27 further comprises one end of a hydraulic double lumen catheter 41, where said catheter 41 engages said bladder at the same one end of grid 20. Moreover, one end of a separate electrical conduit 55, which comprises the lead wires 54, engages at the same end of grid 20. The hydraulic double lumen catheter 41 allows for ingress and egress of fluids into and out of the bladder/cavity and pressure monitoring. The electrical conduit allows for communication of electrophysiological information between the contacted tissue and external apparatus (e.g., EEG monitor).

A second end of the hydraulic double lumen catheter 41 engages a housing 42 containing twin hydraulic connecting ports 44 and 45 (e.g., luer-locks), where one connecting port is separately attached to one lumen comprising the hydraulic double lumen 41.

Further, one of the twin hydraulic connectors 44 is used for the evacuation of air bubbles in the hydraulic conduit 41 through the stopcock 46. Moreover, the other member of the twin connectors 45 (i.e., for connecting to hydraulic pressure recording apparatus) is connected to a strain gauge apparatus 81 via a male luer-lock connector 82. Said gauge apparatus 81 comprises a conventional output display, monitor and suitable power source.

A second end of the electrical conduit 55 comprises a contact/connector for external apparatus such as an EEG device, where the tail comprises a cable assembly 56. The contacts on the cable assembly 56 engage the EEG cable assembly connecting block 62, where the block engages connecting wires 63 (which includes male EEG input pin jack 64) of the EEG cable assembly via connecting pins 61. Further, said input pin jack 64 electrically connects to a conventional EEG, where said EEG comprises a conventional output display, monitor and suitable power source.

At least one of the connecting wires 63 of the EEG cable assembly electrically connects to a DC amplifier 96 at electrical connection 98. A platinum needle electrode 58 also electrically connects to the DC amplifier 96. Said DC amplifier 96 comprises a conventional output display, monitor and suitable power source. Moreover, at least one of the connecting wires 63 of the EEG cable assembly electrically may connect to a separate external apparatus 100, wherein apparatus 100 comprises a conventional output display, monitor and suitable power source.

Such a set up allows for real-time monitoring of electrophysiological responses of the brain during pre- and post-operative procedures.

Figure 8A:
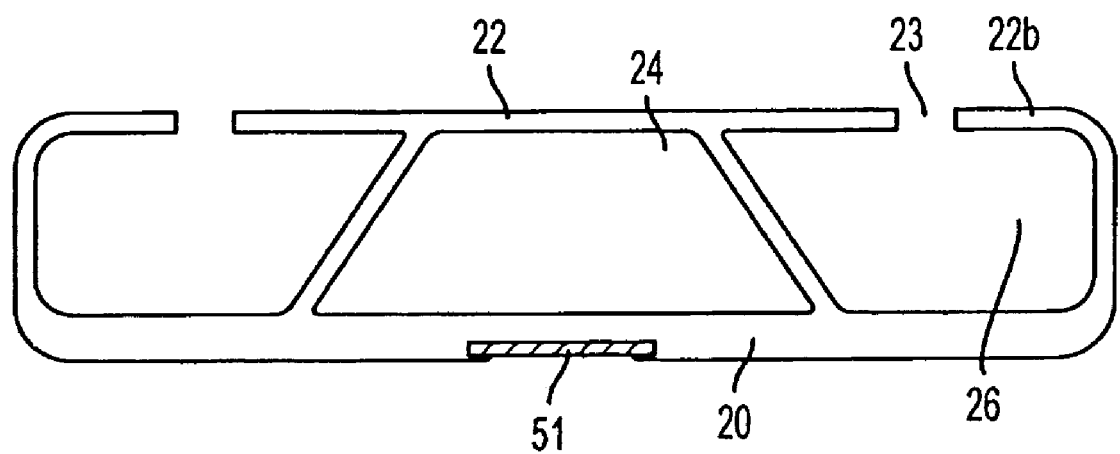
FIG. 8A Cross-sectional view of SS at point A in FIG. 7.

In FIG. 8A, a cross-sectional view of the SS 12 is illustrated from the perspective from point A of FIG. 7.

A detailed view of the fluid-filled (expanded) bladder/cavity 24 is shown in FIG. 8A, including the roof 22 and the bladder/cavity 24 of the elastomer grid 20. Further, a partially exposed electrode 51 which makes contact with the tissue (i.e., the brain) is also shown.

The contours of the perforated drain comprising the grid 12 is also shown in the cross-sectional view of FIG. 8A, such is represented by the opening on the outer surface of grid 12 at 23 (to include the roof of said drain at 22b), where 23 allows evacuation of residual fluid into the lumen 26.

Figure 8B:
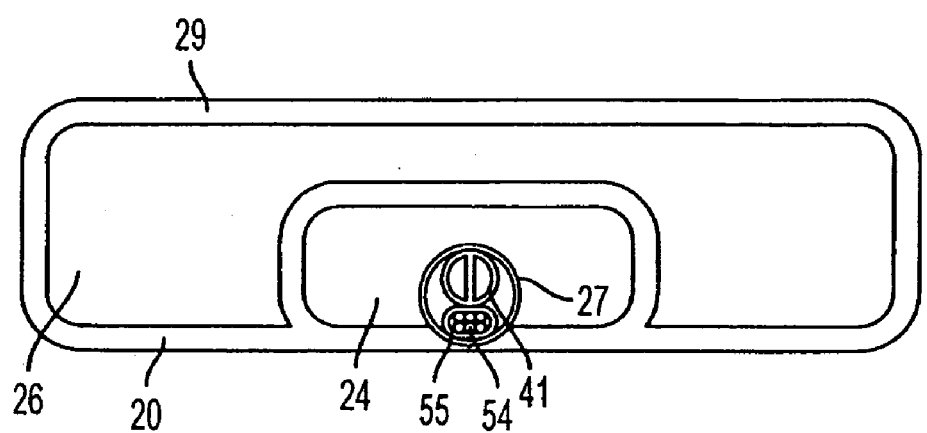
FIG. 8B Cross-sectional view of SS at point B in FIG. 7.

In FIG. 8B, the cross-sectional view of the SS 12 is illustrated from the perspective from point B of FIG. 7.

A detailed view of the fluid-filled (expanded) bladder/cavity 24 is shown in FIG. 8B, including the sheathing conduit 29, bladder/cavity 24, which has tapered here from its more distal width, and drain lumen 26 of the elastomer grid 20. Further, a cross-section of conduit 27, which sheathes the hydraulic double lumen catheter 41 and electrical conduit 55 is also shown.

Cross-sectional detail of the sheathing-conduit 27 illustrates the inner lumenal surfaces of the double lumen catheter 41 and the electrical conduit 55, including the coated wire leads 54. The lumens each serve separate purposes; i.e., one lumen is for the evacuation of gases such that there are no air bubbles present in the conduit and cavity/bladder, and the other lumen to measure/monitor pressure.

Figure 8C:
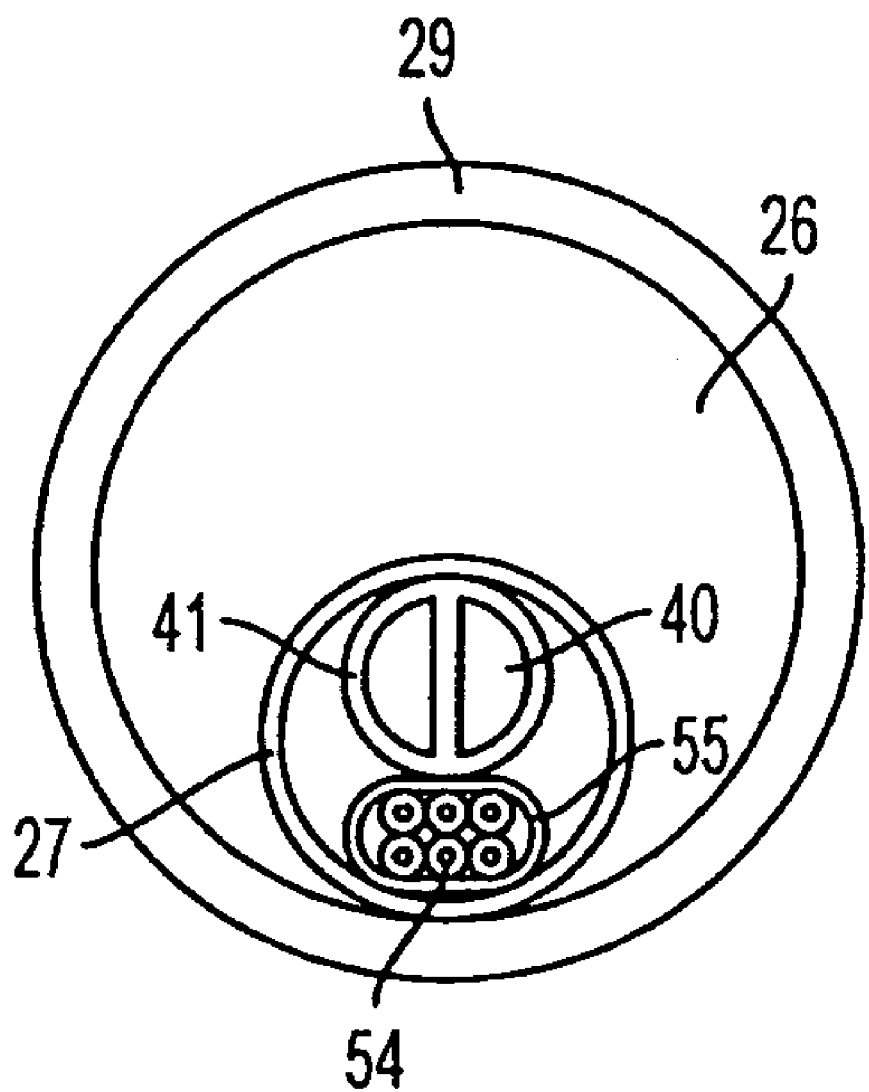
FIG. 8C Cross-sectional view of SS exiting conduit at point C in FIG. 7.

In FIG. 8C, the cross-sectional view of the SS 12 is illustrated from the perspective from point C of FIG. 7.

A detailed view of the sheathing conduit 29, comprising drain lumen 26 and conduit 27. Further, a cross-section of conduit 27, which sheathes the hydraulic double lumen catheter 41 and electrical conduit 55 is also shown.

Cross-sectional detail of the sheathing-conduit 27 illustrates the inner lumenal surfaces of the double lumen catheter 41 and the electrical conduit 55, including separate, coated wire leads 54. The lumens (40) each serve separate purposes; i.e., one lumen is for the evacuation of gases such that there are no air bubbles present in the conduit and cavity/bladder and the other lumen to measure/monitor pressure.

Figure 9A:
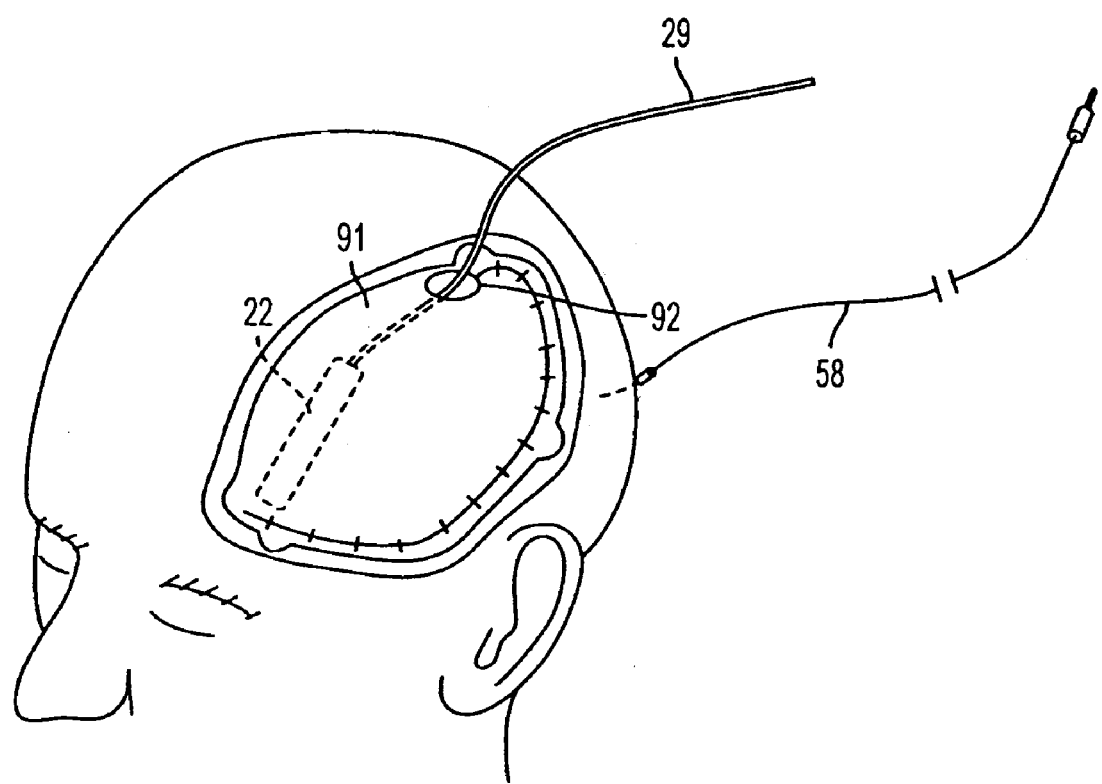
FIG. 9A Perspective view of subdural placement of intracranial sensor for either stage I of epilepsy surgery or for surgery for head trauma. Scalp flap and removed bone flap are not shown.

FIG. 9A is a perspective view of an intracranial sensor placed subdurally (e.g., SS 12) for surgery, where the scalp and bone flaps are not shown. The figure shows the roof of the cavity/bladder 22, the dura mater 91 and opening of dura mater 92 permitting exit of the sheathing conduit 29 and the a platinum needle reference electrode 58.

Figure 9B:
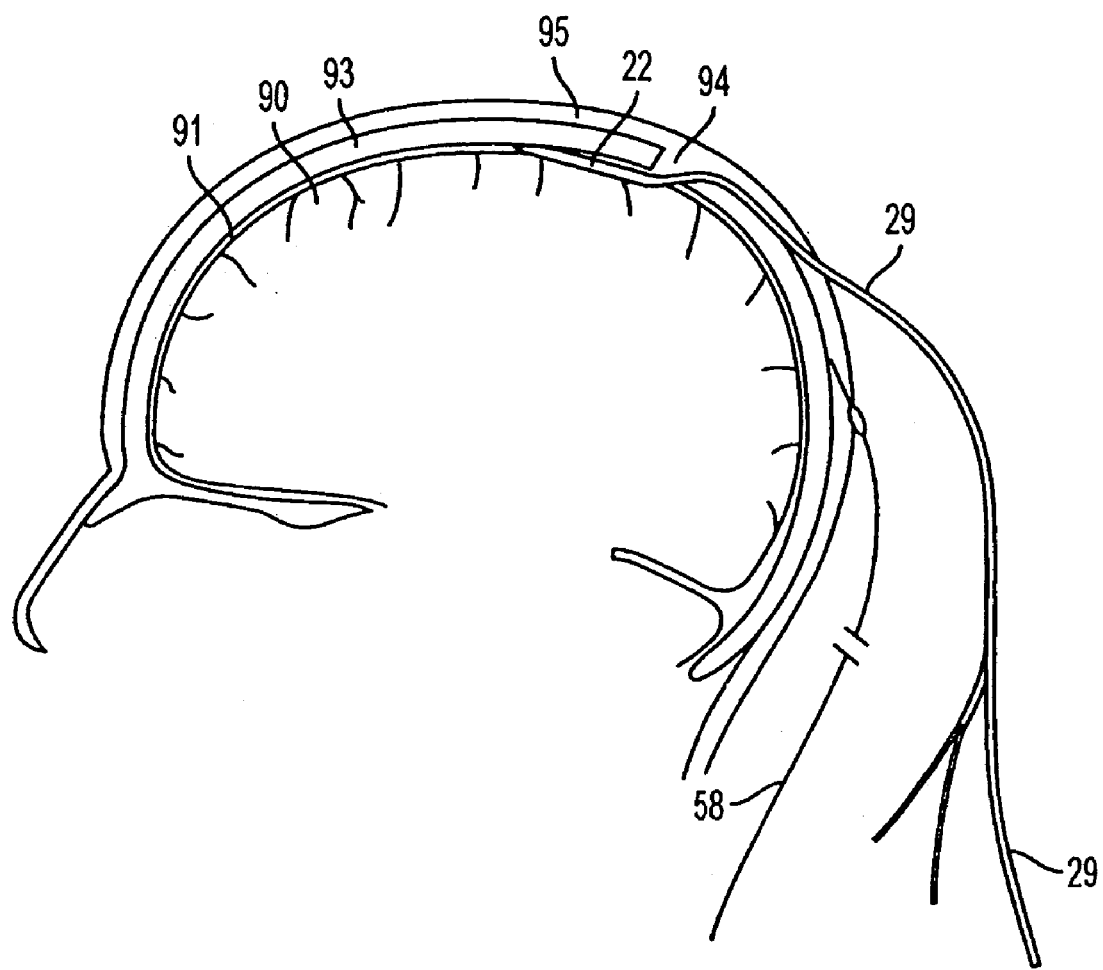
FIG. 9B Sagittal section view of intracranial sensor placed subdurally, as in FIG. 7A. Pt needle reference electrode also shown. Exit of conduit is via a burr hole in calvarium.

FIG. 9B is a sagittal view of an intracranial sensor placed subdurally (e.g., SD 12). The figure shows the roof of the cavity/bladder 22, the dura mater 91, cerebral tissue 90, the calvarium 93, the scalp 95 and a burr hole in the calvarium permitting exit of conduit 29.

While this invention has been described in connection with various embodiments, alternative physical configurations of the devices are envisaged by the present invention.

The following example is included for purposes of illustrating certain aspects of the invention and should not be construed as limiting.

EXAMPLES

Example I

A series of experiments was carried out in anesthetized New Zealand white rabbits in order to evaluate the function of the BRS. Rabbits were placed in a stereotactic head frame, and a temporo-parietal craniotomy was performed using a high-speed surgical drill. Using a retractor blade with BRS mounted to a micromanipulator, groups of animals underwent medially-directed retraction of the lateral temporal lobe at an initial pressure of 20, 30 or 40 mm Hg, as gauged by the device, for either 15 or 30 min. Electrocorticogram (ECoG), which refers to EEG taken directly from the cortical surface rather than scalp, along with cortical DC potential and retraction pressure were recorded on a Bio-logic digital polysomnographic monitor during the retraction period and for 8 hours post-injury. The latter two modalities were amplified via a battery-powered Iso-Dam® high-input impedance DC amplifier (World Precision Instruments, Sarasota, Fla.) and catheter strain gauge with bridge amplifier (TransBridge, World Precision Instruments, Sarasota, Fla.), respectively. The reference electrode for DC potential was placed in trapezius muscle. At the conclusion of the experiment, the brains were removed, sectioned in 2 mm slices, and stained to permit volumetric quantitation of histopathologic injury.

Figure 10:
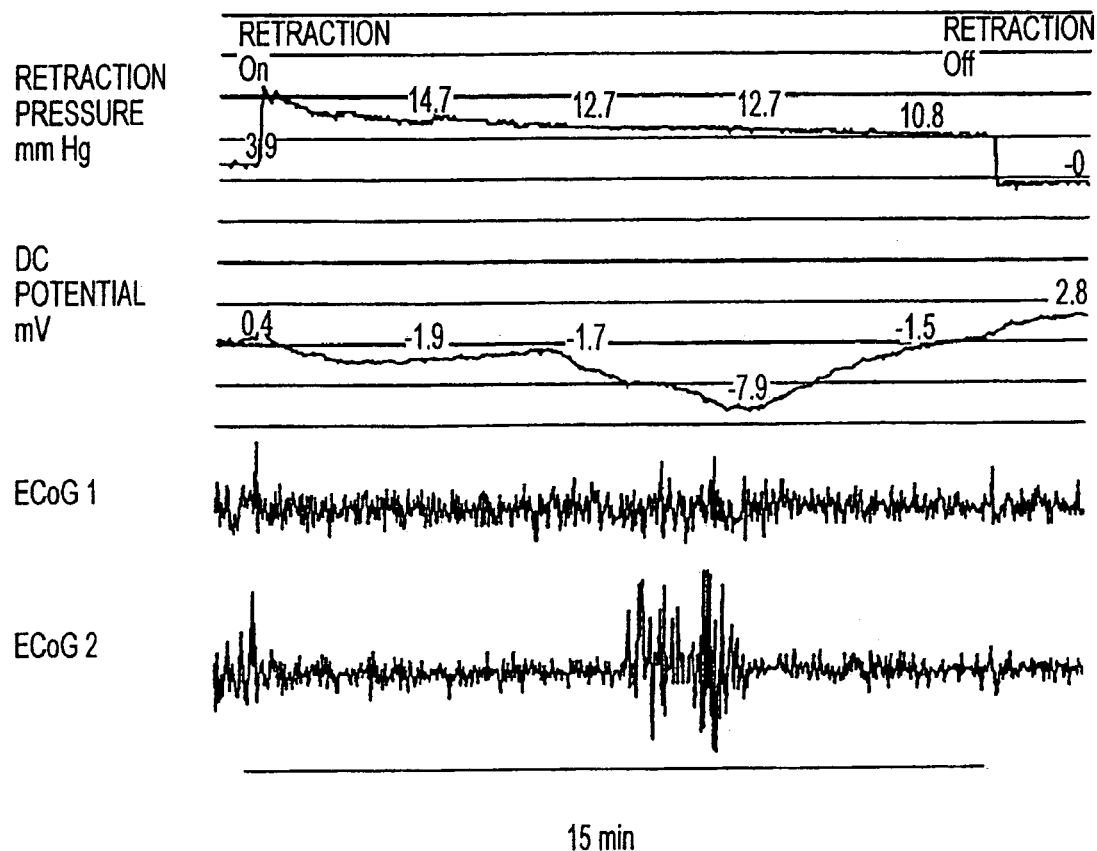
FIG. 10 Digital recording of data obtained from the BRS during medial retraction of the temporal lobe in an experimental rabbit. DC potential and electrocorticograph (EcoG) were recorded from the distal most platinum contact.

FIG. 10 illustrates the recorded data during retraction from a typical experiment where the temporal lobe was retracted to an initial pressure of 20 mm Hg for 15 minutes. Prior to retraction, the resting pressure of the blade against the brain was 3.9 mm Hg. The decay of retraction pressure to about 50% of initial pressure seen in this figure is typical, and is believed to be due to local redistribution of blood volume in the cerebral hemisphere secondary to compression. Minutes after the onset of retraction, the negative DC potential shift is apparent from the tracings. Because the degree of retraction in this particular experiment is relatively mild, normalization of the negative DC shift actually starts prior to the conclusion of the retraction period, unlike that seen with more severe retraction. In the ECoG2 channel, recorded from the second most distal contact of the BRS, an epileptiform spike discharge occurs at about the time of the peak of the DC shift. This type of activity is not uncommon during retraction of the temporal lobe in this animal model. This particular animal demonstrated a fairly mild degree of histopathologic injury compared to other rabbits in the study.

Using the sensor, the data from this investigation demonstrates significant regression correlations between retraction pressure (in terms of the pressure-time integral, which takes the decay into account) and both the severity of the negative DC potential shift as well as the volume of histopathologic injury. A similar type of study using the BRS is also being carried out in patients undergoing surgery for aneurysm clipping or resection of skull-base tumors. Rather than by quantitation of histologic damage, in this study injury is assessed in terms of radiographic signal abnormality and presence or absence of clinical deficit referable to retraction postoperatively. This analysis will hopefully permit the establishment of criteria for retraction injury threshold based on retraction pressure-duration and electrocortical parameters. Currently, such guidelines do not exist.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

I claim:

1. A brain retractor device comprising:
   a first end comprising a substantially inextensible first cavity, wherein said first end is integral with a retractor blade;
   a plurality of electrodes exposed along a first surface of said first end; a first electric conduit;
   a second conduit, which said second conduit allows for measuring pressure; and
   a second end comprising an exit port, which exit port engages said first and second conduit.

2. The device of claim 1, wherein said electrodes are polarizable or non-polarizable.

3. The device of claim 2, wherein said electrodes are non-polarizable.

4. The device of claim 3, further wherein a distal end of said first electric conduit and one end of a remote reference electrode electrically connect to a differential DC amplifier.

5. The device of claim 1, wherein said second conduit is hydraulic.

6. The device of claim 1, wherein said retractor blade comprises a first aperture, which first aperture allows said first and second conduits to traverse opposing blade surfaces.

7. The device of claim 1, wherein said first end comprises substantially flat, smooth atraumatic faces.

8. The device of claim 1, wherein said first end comprises a thin, elastically deformable, bio-compatible material.

9. The device of claim 8, wherein the bio-compatible material is selected from silicone-based materials, thermoplastic elastomer, low density polyethylene or polyurethane.

10. The device of claim 1, wherein the exposed outer surface of the first cavity extends beyond the edges of the retractor blade.

11. The device of claim 10, wherein the extended surface does not obscure the operative field.

12. The device of claim 10, wherein said first cavity comprises a bladder or a network of interconnected lumens internal to the exposed surface.

13. The device of claim 1, wherein said device is able to operate whether the first cavity is filled with a gas or a liquid.

14. The device of claim 13, wherein the first cavity is filled with a gas.

15. The device of claim 13, wherein the first cavity is filled with a liquid.

16. The device of claim 15, wherein the liquid is selected from normal saline, buffered salt solution, Ringer's solution, Elliot's B solution, or mock cerebrospinal fluid.

17. The device of claim 1, wherein the cavity comprises a heat exchange fluid for induction of local brain hypothermia for the purpose of neuroprotection.

18. The device of claim 17, wherein said fluid is cooled by extracorporeal refrigeration.

19. The device of claim 18, wherein the fluid is cooled to a temperature of between about 0° C. to about 10° C.

20. The device of claim 17, wherein the heat exchange fluid is selected from saline, lactated Ringer's solution, water, Elliot's B solution or mock cerebrospinal fluid.

21. The device of claim 1, wherein said electric conduit further comprises a first tail distal to said first end, wherein said tail allows for communication between the device and at least one peripheral apparatus.

22. The device of claim 21, wherein the peripheral device comprises at least one adjunctive monitoring modality.

23. The device of claim 22, wherein said modality measures physiological parameters selected from brain compliance or elastance, cerebral impedance, fluid flow, partial pressure of oxygen or carbon dioxide, temperature, pH, metabolites or a combination thereof.

24. The device of claim 23, wherein said fluid flow is blood flow.

25. The device of claim 23, wherein said metabolites are selected from extracellular potassium or glutamate.

26. The device of claim 1, wherein said second conduit comprises a flexible, noncompliant material.

27. The device of claim 26, wherein said second conduit comprises at least one luminal surface.

28. The device of claim 27, wherein said second conduit comprises a double lumen catheter.

29. The device of claim 28, wherein one end of each separate luminal surface comprising said double lumen catheter engages separate fluid-flow directing connectors.

30. The device of claim 29, wherein said fluid-flow connectors are female luer-lock connectors.

31. The device of claim 1, wherein said first cavity can accommodate pressures of between about one mm Hg and about 120 mm Hg.

32. The device of claim 1, wherein the refractor blade comprises a substantially polygonal shape.

33. The device of claim 32, wherein the polygonal shape is substantially quadrilateral, further comprising rounded edges at straight-line boundaries.

34. The device of claim 32, wherein the retractor blade is tapered or blunt.

35. The device of claim 1, wherein said device is a brain retractor sensor (BRS).

36. A sub-dural device comprising:
a first end comprising a substantially inextensible cavity;
a plurality of electrodes exposed along a first surface of said first end;
a first electric conduit;
a second conduit, which said second conduit allows for measuring pressure; and
a second end comprising an exit port, which exit port engages said first and second conduit,
wherein said device is able to operate whether the cavity is filled with a gas or a liquid.

37. The device of claim 36, wherein said electrodes are polarizable or non-polarizable.

38. The device of claim 37, wherein said electrodes are non-polarizable.

39. The device of claim 38, further wherein a distal end of said first electric conduit and one end of a remote reference electrode electrically connect to a differential DC amplifier.

40. The device of claim 36, wherein said second conduit is hydraulic.

41. The device of claim 36, wherein said first end comprises substantially flat, smooth atraumatic faces.

42. The device of claim 36, wherein said first end comprises a thin, elastically deformable, bio-compatible material.

43. The device of claim 42, wherein the bio-compatible material is selected from silicone-based materials, thermoplastic elastomer, low density polyethylene or polyurethane.

44. The device of claim 43, wherein said cavity comprises a bladder or a network of interconnected lumens internal to the exposed surface.

45. The device of claim 36, wherein the cavity is filled with a gas.

46. The device of claim 36, wherein the cavity is filled with a liquid.

47. The device of claim 46, wherein the liquid is selected from normal saline, buffered salt solution, Ringer's solution, Elliot's B solution or mock cerebrospinal fluid.

48. The device of claim 36, wherein the cavity comprises a heat exchange fluid for induction of local brain hypothermia for the purpose of neuroprotection.

49. The device of claim 48, wherein said fluid is cooled by extracorporeal refrigeration.

50. The device of claim 49, wherein the fluid is cooled to a temperature of between about 0° C. to about 10° C.

51. The device of claim 50, wherein the heat exchange fluid is selected from saline, lactated Ringer's solution, water, Elliot's B solution or mock cerebrospinal fluid.

52. The device of claim 36, wherein said first electric conduit further comprises a first tail distal to said first end, wherein said tail allows for communication between the device and at least one peripheral apparatus.

53. The device of claim 52, wherein the peripheral device comprises at least one adjunctive monitoring modality.

54. The device of claim 53, wherein said modality measures physiological parameters selected from brain compliance or elastance, cerebral impedance, fluid flow, partial pressure of oxygen or carbon dioxide, temperature, pH, metabolites or a combination thereof.

55. The device of claim 54, wherein said fluid flow is blood flow.

56. The device of claim 54, wherein said metabolites are selected from extracellular potassium or glutamate.

57. The device of claim 36, wherein said second conduit comprises a flexible, noncompliant material.

58. The device of claim 57, wherein said second conduit comprises at least one luminal surface.

59. The device of claim 58, wherein said second conduit comprises a double lumen catheter.

60. The device of claim 59, wherein one end of each separate luminal surface comprising said double lumen catheter engages separate fluid-flow directing connectors.

61. The device of claim 60, wherein said fluid-flow connectors are female luer-lock connectors.

62. The device of claim 36, wherein said cavity can accommodate pressures of between about one mm Hg and about 120 mm Hg.

* * * * *